United States Patent
Jiles et al.

(10) Patent No.: US 9,488,537 B2
(45) Date of Patent: Nov. 8, 2016

(54) SYSTEM AND METHOD FOR DETERMINING STRESS OF A COMPONENT MADE OF MAGNETIZABLE MATERIAL

(75) Inventors: David C. Jiles, Samarate (IT); Lukasz Mierczak, Samarate (IT); Luigi Merletti, Samarate (IT); Gabriele Fantoni, Samarate (IT)

(73) Assignee: AGUSTA WESTLAND S.P.A., Samarate (IT)

( * ) Notice: Subject to any disclaimer, the term of this patent is extended or adjusted under 35 U.S.C. 154(b) by 872 days.

(21) Appl. No.: 13/699,128

(22) PCT Filed: May 23, 2011

(86) PCT No.: PCT/IB2011/001105
§ 371 (c)(1),
(2), (4) Date: Jan. 18, 2013

(87) PCT Pub. No.: WO2011/144998
PCT Pub. Date: Nov. 24, 2011

(65) Prior Publication Data
US 2013/0116938 A1    May 9, 2013

(30) Foreign Application Priority Data

May 21, 2010 (IT) .............................. TO20100095 U

(51) Int. Cl.
| | |
|---|---|
| *G01N 27/72* | (2006.01) |
| *G01L 1/12* | (2006.01) |
| *G06F 19/00* | (2011.01) |

(52) U.S. Cl.
CPC ................. *G01L 1/12* (2013.01); *G01L 1/125* (2013.01); *G01N 27/72* (2013.01); *G01N 27/725* (2013.01); *G06F 19/00* (2013.01)

(58) Field of Classification Search
CPC .................................. G06F 19/00; G01L 1/12
USPC ............................................................ 702/42
See application file for complete search history.

(56) References Cited

U.S. PATENT DOCUMENTS

| | | | | |
|---|---|---|---|---|
| 5,166,613 | A | * | 11/1992 | Perry ...................... G01L 1/125 324/209 |
| 5,313,405 | A | * | 5/1994 | Jiles ...................... G01N 27/725 324/209 |
| 2010/0127582 | A1 | * | 5/2010 | Nair ...................... F03D 11/0008 310/26 |

(Continued)

OTHER PUBLICATIONS

C.C.H. Lo, S.J. Lee, L.Li, L.C.Kerdus, and D.C.Jiles; "Modeling Stress Effects on Magnetic Hysteresis and Barkhausen Emission Using a Hysteretic—Stochastic Model"; Sep. 2002; IEEE Transactions on Magnetics; vol. 38, No. 5; pp. 2418-2420.*

(Continued)

*Primary Examiner* — John Breene
*Assistant Examiner* — Christine Liao
(74) *Attorney, Agent, or Firm* — Leason Ellis LLP

(57) ABSTRACT

The present system determines a significant stress value (σ) of a component made of magnetizable material. The system has a generating stage for generating a magnetic field of varying amplitude (H); and also includes a pickup stage for acquiring a Barkhausen noise signal (MBN) alongside variations in the amplitude (H) of the magnetic field. The system is characterized by having a processing unit for calculating the reciprocal (1/MBNmax) of the maximum value (MBNmax) of the signal (MBN), alongside variations in the amplitude (H) of the magnetic field. The processing unit has a memory stage storing a linear relation between the reciprocal (1/MBNmax) of the maximum value and the significant stress value (σ).

14 Claims, 4 Drawing Sheets

(56) References Cited

U.S. PATENT DOCUMENTS

2011/0140691 A1* 6/2011 Roy .................. G01R 33/1223
324/228

OTHER PUBLICATIONS

M.J. Sablik and B. Augustyniak; "Biaxial Stress Effects on Barkhausen Signals in a Steel Pipe for the Case of Magnetic Field Noncoaxial with stress axes"; 1999, Kluwer Academic/Plenum Publishers; Review of Progress in Quantitative Nondestructive Evaluation, vol. 18, pp. 1887-1894.*

Mierczak I et al: "A New Method for 1-15 Evaluation of Mechanical Stress Using the Reciprocal Amplitude of Magnetic Barkhausen Noise", IEEE Transactions on Magnetics, IEEE Service Center, New York, NY, US, vol. 47, No. 2, Feb. 1, 2011 , pp. 459-465, XP011343677.

* cited by examiner

SYSTEM AND METHOD FOR DETERMINING STRESS OF A COMPONENT MADE OF MAGNETIZABLE MATERIAL

TECHNICAL FIELD

The present invention relates to a system and method for determining stress of a component, preferably an aircraft component, made of magnetizable material.

BACKGROUND ART

As is known, the aircraft industry employs nitrided Or carburized steel components, which are first carburized, then shot peened, and finally ground.

Shot peening is a mechanical process of cold working the component surface to produce an isotropic residual compression state in the outermost layers of the component.

Grinding often affects the final surface condition of shot peened components in terms of properties such as residual stress, microstructure, and consequent resistance to wear and fatigue.

In particular, localized immission of energy, in the form of heat produced in the grinding area, can cause serious thermal damage in the surface layer, if grinding parameters are not carefully controlled.

If the temperature of the component exceeds tempering temperature, grinding may produce microstructural martensitic changes at metallurgical level, resulting in so-called overtempered martensite: a metastable phase involving softer surface regions and a general decline in mechanical properties.

As a result, overtempered martensite may accelerate the onset of cracks; and grinding may also alter the residual stress pattern of the material.

In the worst case scenario, the material may present residual compressive stress in the surface region, and residual tensile stress in an inner region close to the surface, thus resulting in abrupt changes in stress of the material.

The ultimate amplitude and uniformity of the stress may vary considerably.

A need is therefore felt within the industry to determine the effect of grinding on the stress of components, to enable an accurate evaluation of the component's resistance to fatigue.

Known chemical etching component inspection methods are only effective for heavy microstructural steels, and invariably involve a certain amount of subjective evaluation.

Moreover, they also fail to determine changes, caused by overtempering, in the residual stress of carburized or nitrided steel components.

An alternative method of determining stress of a component employs the Barkhausen effect.

According to the Barkhausen effect, the magnetic flux inside a component of magnetizable, e.g. ferromagnetic, material exposed to a varying magnetic field does not vary continuously, but goes through discrete changes, which induce, in a coil placed close to the component, voltage pulses that can be amplified and connected to a loudspeaker to generate acoustic pulses known as Barkhausen noise.

The discrete changes in the magnetic flux inside the component are related to discontinuous movements of the magnetic domain edges. More specifically, in a nonmagnetized component, the magnetic domains are oriented randomly, so mean magnetization of the body is zero. When exposed to an external magnetic field, the orientation of the component's domains tends to change accordingly, and goes through the movement of the adjacent domain walls, so 'macroscopic' magnetization of the body goes through discrete changes owing to the magnetic discontinuities within the component.

Barkhausen noise characteristics are known to be affected by tensile or compressive stress of the component.

A need is felt within the industry for a system and method for determining stress of a component made of magnetizable material using the Barkhausen effect, and which are easy to implement.

A need is also felt for a straightforward, easy-to-implement system and method for determining said stress at different component depths.

DISCLOSURE OF INVENTION

According to the present invention, there is provided a system for determining stress of a component made of magnetizable material, the system comprising:
 a generating stage for generating a magnetic field of varying amplitude; and
 a pickup stage for acquiring a Barkhausen noise signal alongside variations in said amplitude of said magnetic field;
 the system being characterized by comprising a processing unit for calculating the reciprocal of the maximum value of said signal, alongside variations in said amplitude of said magnetic field;
 said processing unit comprising a memory stage storing a linear relation between said reciprocal of said maximum value and a significant stress value.

According to the present invention, there is also provided a method of determining stress of a component made of magnetizable material, the method comprising the steps of:
 generating a magnetic field of varying amplitude; and
 acquiring a Barkhausen noise signal of said component alongside variations in said amplitude of said magnetic field;
 the method being characterized by comprising the steps of:
 calculating the reciprocal of the maximum value of said Barkhausen noise signal, alongside variations in said amplitude of said magnetic field; and
 calculating a significant stress value of said component by means of a linear relation between said reciprocal of the maximum value and the significant stress value.

BRIEF DESCRIPTION OF THE DRAWINGS

A preferred, non-limiting embodiment of the present invention will be described by way of example with reference to the accompanying drawings, in which.

BEST MODE FOR CARRYING OUT THE INVENTION

Figure 1:
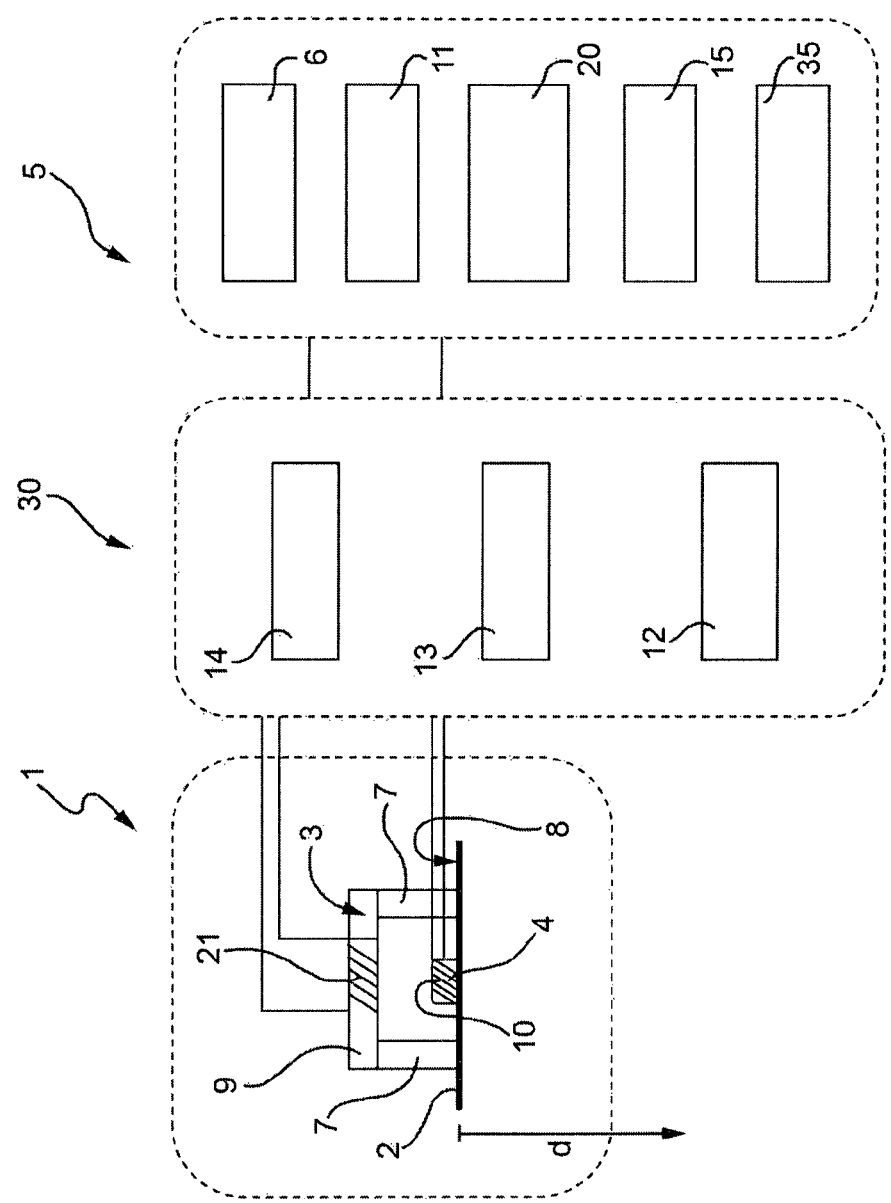
FIG. 1 shows a schematic of a system, in accordance with the present invention, for determining stress of a component made of magnetizable material.

Number 1 in FIG. 1 indicates as a whole a system for determining stress of a component 2 made of magnetizable, preferably ferromagnetic, material.

Component 2 is preferably an aircraft component.

Component 2 has preferably been hardened by heat treatment, shot peening, and grinding.

Component 2 is also preferably made of carburized or nitrided steel, and has been ground above tempering temperature.

System 1 substantially comprises:
- a magnetizing element 3 for generating on component 2 an alternating magnetic field with different frequency values f1, f2, . . . , fi, . . . fn and different amplitude values H;
- a probe 4 for determining the effective value MBN of the amplitude of the Barkhausen noise derived from the action of the magnetic field within component 2; and
- a processing unit 5 for processing the Barkhausen noise acquired by probe 4, and issuing a significant value σ of the stress in component 2.

More specifically, element 3 is preferably a ferrite core fitted with a winding 21 connected to an alternating-current generator 6.

Element 3 is U-shaped, and comprises two parallel arms 7 with respective ends contacting and perpendicular to a free surface 8 of component 2; and a crosspiece 9 extending between arms 7 and parallel to and a given distance from surface 8.

The magnetic field generated by element 3 induces a discretely-varying magnetic flux in component 2.

Probe 4 comprises a winding 10, in which the perpendicular component of the magnetic flux between the two opposite arms 7 is acquired. The same magnetic flux is present in component 2, and generates discrete jumps in voltage of effective value MBN.

For each frequency f1, f2, . . . , fi, . . . , fn, processing unit 5 calculates the maximum value MBNmax of effective value MBN alongside variations in the amplitude H of the magnetic field applied by element 3.

System 1 also comprises:
- an amplifier 12 for amplifying the effective value MBN acquired by probe 4; and
- a band-pass filter 11 for filtering effective value MBN.

More specifically, filter 11 is designed to pass the frequency components of effective value MBN between:
- frequency f1, f2, . . . , fi, . . . , fn associated with a respective distance d1, d2, . . . , di, . . . dn between surface 8 and the examination region of component 2; and
- a threshold frequency fo independent of the distance from surface 8.

More specifically, frequency fi equals:

$$fi = \frac{1}{\pi \sigma_e \mu (di^2)} \quad (1)$$

where $\mu = \mu_0 \mu_r$ is magnetic permeability, $\sigma_e$ is electric conductivity, and di is the distance from surface 8 of component 2, at which the significant stress value σ is determined.

Each frequency f1, f2, . . . , fi, . . . , fn therefore corresponds to a given penetration of the magnetic field to a different distance d1, d2, . . . , di, . . . , dn from and measured perpendicular to surface 8.

More specifically, the more frequency f1, f2, . . . , fi, . . . , fn decreases, the more distance d1, d2, . . . , di, . . . , dn increases.

Processing unit 5 is advantageously configured to calculate the reciprocal 1/MBNmax of maximum value MBNmax of effective value MBN alongside variations in the amplitude H of the magnetic field, for each frequency f1, f2, . . . , fi, . . . , fn corresponding to a respective distance d1, d2, . . . , di, . . . , dn, and comprises a memory stage 15 storing, for each frequency f1, f2, . . . , fi, . . . , fn, a linear relation (FIGS. 6 and 9) between the reciprocal (1/MBNmax) of maximum value MBNmax of effective value MBN, and a significant stress value σ.

Significant value σ equals the tensile or compressive stress, in the case of monoaxial stress, or the equivalent stress, in the case of multiaxial stress.

Each linear relation therefore shows the relationship between the reciprocal (1/MBNmax) of maximum value MBNmax and significant stress value σ at a different distance di from surface 8.

System 1 also comprises an analysis stage 20 for subtracting, from the effective value MBN acquired at distance di, a significant value of the effective values MBN acquired at distances d1, d2, . . . , di-1 smaller than distance di.

Said significant value preferably equals the effective value MBN acquired at distance di-1.

System 1 thus factors in attenuation of effective value MBN caused by distance di between surface 8 and the region of component 2 in which significant stress value σ is measured.

Memory stage 15 preferably stores a number of first linear relations (one shown in FIG. 5) between reciprocal 1/MBNmax and significant applied-stress value σ, for respective frequencies f1, f2, . . . , fi, . . . , fn.

Memory stage 15 also stores a number of second linear relations (two shown in FIG. 9) between reciprocal 1/MBNmax and significant residual-stress value σ, for respective frequencies f1, f2, . . . , fi, . . . , fn.

The angular coefficients of said relations are preferably equal for the same frequency values f1, f2, . . . , fi, . . . , fn.

The graph of each linear relation stored in memory stage 15 is obtained when calibrating system 1.

At the calibration stage, significant value σ for a given material and a given distance di is determined by x-ray diffractometry, and reciprocal 1/MBNmax is determined for each significant stress value σ.

Amplifier 12, a data acquisition card 13, and a power amplifier 14 for element 13 are installed in a central unit 30 of system 1.

Generator 6, filter 11, memory stage 15, analysis stage 20, and a display stage 35, for displaying significant value σ, are installed in a personal computer of system 1.

Software, loaded and executed on processing unit 5, employs an algorithm which generates the value of reciprocal 1/MBNmax and the corresponding significant value o for each frequency fi.

In actual use, element 3 generates a variable magnetic field with a given frequency f1, f2, . . . , fi, . . . , fn. And the amplitude H of the magnetic field is varied, while maintaining frequency f1, f2, . . . , fi, . . . , fn constant.

On striking component 2, the magnetic field aligns the magnetic domains of component 2, thus producing discrete voltage pulses of effective value MBN in winding 10 of probe 4.

Filter 11 filters the voltage signal of effective value MBN.

For each frequency value f1, f2, . . . , fi, . . . , fn, processing unit 5 calculates the maximum value MBNmax of effective values MBN alongside variations in amplitude H of the magnetic field, and, on the basis of the linear relations (FIGS. 5 and 9) in memory stage 15, generates the significant stress value o of component 2 at the distance di associated with frequency f1, f2, . . . , fi, . . . , fn.

Frequency f1, f2, . . . , fi, . . . , fn is then changed, and the measurement is repeated, as described above, to obtain the significant stress value σ of component 2 at a different distance d1, d2, . . . , di, . . . , dn, using a different linear relation stored in memory stage 15.

For each distance di, analysis stage 20 subtracts, from the effective values MBN acquired at distance di, a significant value of the effective values MBN acquired at distances d1, d2, . . . , di-1, to factor in Barkhausen noise attenuation by the material of component 2 at distances d1, d2, . . . , di-1 smaller than distance di from surface 8.

The significant value preferably equals the effective value MBN acquired at distance di-1.

Before measuring significant value σ, system 1 is calibrated by memorizing the linear relations in memory stage 15.

More specifically, a test-piece made of the same material as component 2 is stressed, and, for each distance di from surface 8:
significant stress value a is measured by x-ray diffractometry; and
maximum value MBNmax is measured by probe 4.

Figure 5:
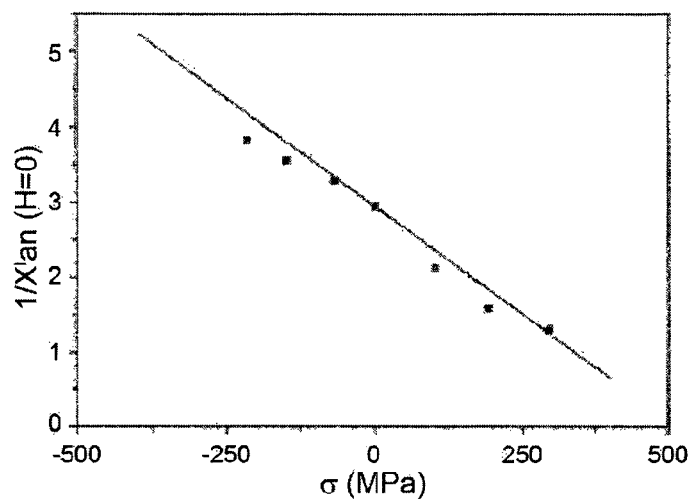
FIG. 5 shows a theoretical test graph of the reciprocal of the nonhysteretic differential susceptibility graph alongside variations in the significant applied-stress value, and for the same component as in FIGS. 2, 3 and 4.
Figure 9:
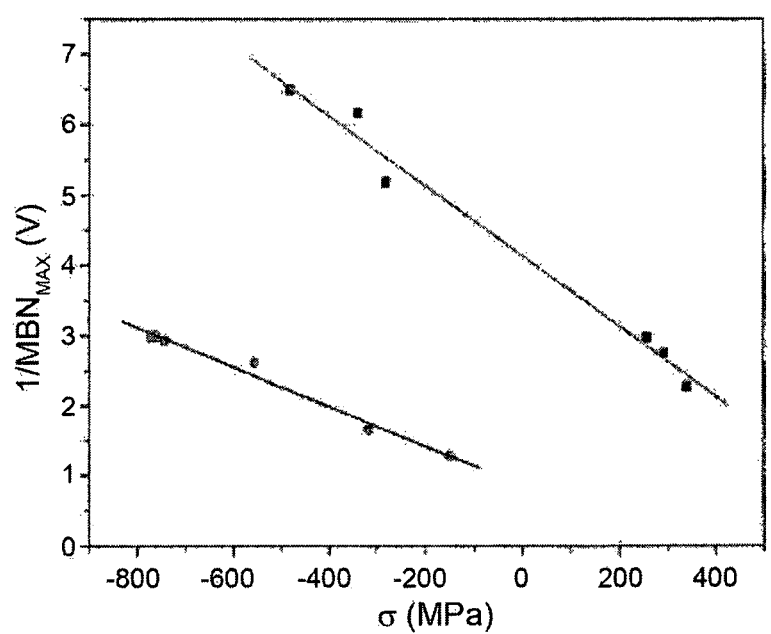
FIG. 9 shows a graph of the reciprocal of the maximum effective Barkhausen noise signal value alongside variations in the significant residual-stress value, and for the same components as in FIGS. 7 and 8.

The linear relations are shown in FIGS. 5 and 9, and are the result of research by the Applicant as described below.

Very briefly, the Applicant has observed that:
for a given material, the maximum value MBNmax of effective value MBN at a given frequency fi depends on maximum differential susceptibility $\chi'_{max}$;
for most materials, nonhysteretic differential susceptibility $\chi'_{an}$ equals maximum differential susceptibility $\chi'_{max}$; and
the reciprocal $1/\chi'_{an}$ of nonhysteretic differential susceptibility $\chi'_{an}$ is a linear function of significant stress value o of the material.

More specifically, maximum nonhysteretic differential susceptibility $\chi'_{an}$ is normally reached at the coercive point, i.e. when amplitude H of the applied magnetic field is zero, and component 2 contains residual magnetization caused by the hysteresis cycle of the material of component 2.

The Applicant has therefore deduced, and confirmed by testing, the existence of a linear relationship between the reciprocal 1/MBNmax of maximum value MBNmax and significant value σ.

More specifically, the Applicant ground cylindrical test-pieces of SAE 9310 and SAE 32CDV13 steel, together with a round, dog-bone-shaped tensile test-piece of SAE 9310 steel, to obtain different conditions on the worked surfaces.

Their chemical compositions are shown in Table 1.

TABLE 1

| | C | Mn | Si | P | S | Cr | Ni | Mo | Cu |
|---|---|---|---|---|---|---|---|---|---|
| SAE 9310 | 0.07–0.13 | 0.04–0.07 | 0.15–0.35 | 0–0.015 | 0–0.015 | 1–1.4 | 3–3.5 | 0.08–0.15 | 0–0.3.5 |

| | C | Mn | Si | P | S | Cr | Ni | Mo | V |
|---|---|---|---|---|---|---|---|---|---|
| 32CDV13 | 0.29–0.36 | 0.4–0.7 | 0.1–0.4 | 0–0.015 | 0–0.005 | 2.8–3.3 | 0.3 | 0.7–1.2 | 0.15–0.35 |

Three 32CDV13 test-pieces and the tensile test-piece were then shot peened to study the high-compressive-stress regions. Details of the dimensions, grinding and shot peening conditions, and resulting residual surface stress of these test-pieces are shown in Tables 2 and 3.

TABLE 2

| SAE 9310 | Diameter per lenght (mm) | Grinding speed (rpn) | Feed speed (rpm) | Lubrication (%) | Residual stress (MPa) |
|---|---|---|---|---|---|
| Test piece 1 | 25 × 35 | 25 | 0.15 | 0 | +399 |
| Test piece 2 | 25 × 35 | 24 | 0.1 | 0 | +292 |
| Test piece 3 | 25 × 35 | 24 | 0.15 | 0 | +256 |
| Test piece 4 | 25 × 35 | 24 | 0.002 | 50 | −281 |
| Test piece 5 | 25 × 35 | 24 | 0.04 | 50 | −339 |
| Test piece 6 | 25 × 35 | 95 | 0.002 | 100 | −482 |
| Tensile test piece | 10 × 50 (usable section) | 95 | 0.002 | 100 | −805 (after shoot peening) |

TABLE 3

| 32CDV13 | Diameter per lenght (mm | Grinding speed (rpn)) | Feed speed (rpm) | Shot peening parameters | Residual stress (MPa) |
|---|---|---|---|---|---|
| Test piece 1 | 30 × 110 | 30 | 0.5 | All test-pieces were shot peened using SAE170, HRC42-52 shot at 0, 008-0, 012A | −145 |
| Test piece 2 | 30 × 110 | 30 | 1.5 | | −298 |
| Test piece 3 | 30 × 110 | 30 | 1 | | −533 |
| Test piece 4 | 30 × 110 | 30 | 0.5 | | −745 |
| Test piece 5 | 30 × 110 | 30 | 1.5 | | −765 |
| Test piece 6 | 30 × 110 | 30 | 1 | | −775 |

During tensile testing, the test-pieces were subjected to different significant stress values σ within the elastic limit, using a mechanical servohydraulic test system; and effective value MBN was measured for a monotonically increasing load in increments of 50 MPa.

Figure 2:
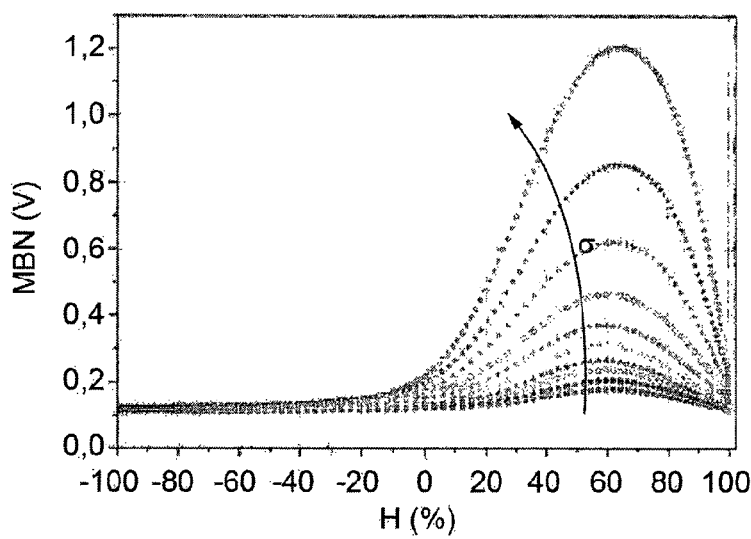
FIG. 2 shows a graph of the effective Barkhausen noise signal value alongside variations in the strength of the magnetic field applied by the FIG. 1 system, and for different significant applied-stress values.

The envelope curves of the sequences of effective values MBN for the carburized SAE 9310 test-piece, and for different significant applied-stress values σ—in this case, tensile stress—are shown in FIG. 2, and represent effective values MBN in the 20 to 1250 kHz frequency range.

A gradual change in the effective Barkhausen noise values MBN was observed in response to a load that generates an increasing significant stress value σ. This behaviour is consistent with the theory that describes the effects of applied stress in terms of an equivalent magnetic field Hσ. This additional field derives from magnetoelastic coupling, and is expressed by the equation:

$$H_\sigma(\theta) = \frac{3}{2}\frac{\sigma}{\mu_0}(\cos^2\theta - \nu\sin^2\theta)\left(\frac{\partial\lambda}{\partial M}\right)_T \quad (2)$$

where σ is the significant stress value; λ is magnetostriction; μ0 is space permeability; θ is the angle between the stress axis (e.g. the pull axis, in the case of tensile stress) and the direction of Hσ; and ν is the Poisson ratio. Effective value MBN is therefore the response to an actual magnetic field which may be expressed as:

$$He = H + H_\sigma + \alpha M \quad (3)$$

where He is the overall magnetic field; α is the mean field parameter representing domain coupling; and Hσ is the equivalent stress field. In the Applicant's measurements, the external magnetic field H applied was coaxial with significant applied-stress value σ, so an increase in significant applied-stress value σ produces a higher overall magnetic field He at the domains.

As a result of this, the domain walls may break the local energy barriers at lower amplitude H values of the applied magnetic field, which is consistent with an increase in the amplitude of effective value MBN.

Figure 3:
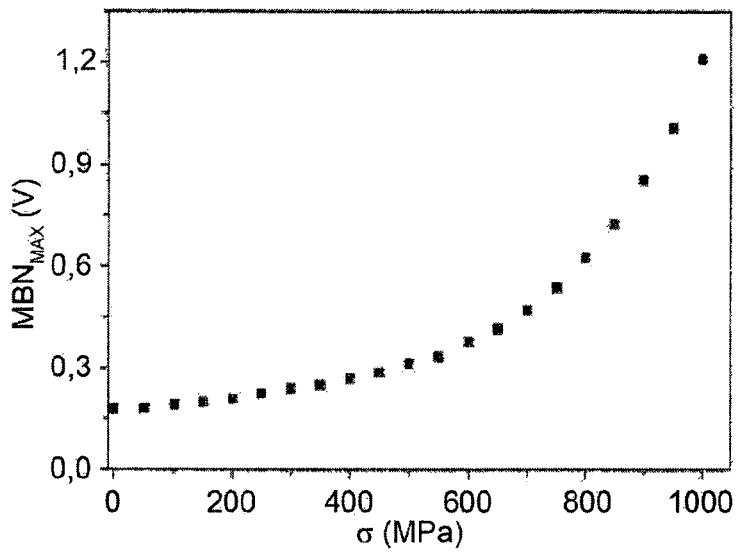
FIG. 3 shows a graph of the effective value of the FIG. 2 Barkhausen noise signal alongside variations in a significant applied-stress value, and for the same component as in FIG. 2.
Figure 4:
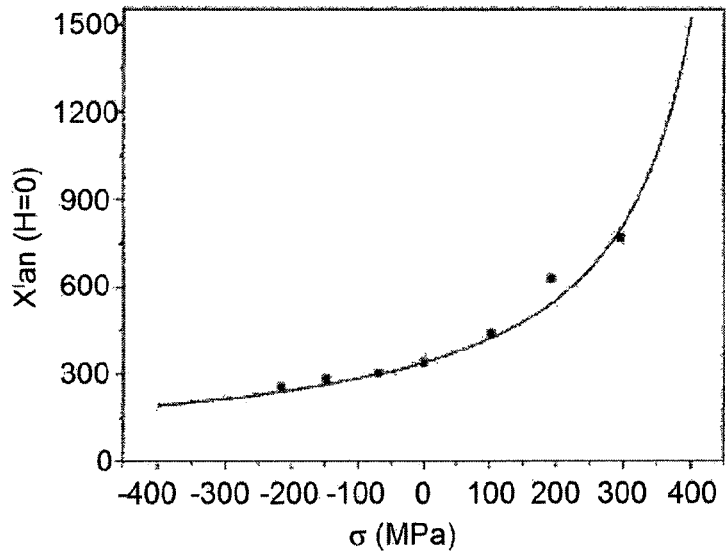
FIG. 4 shows a theoretical test graph of nonhysteretic differential susceptibility at the coercive point, alongside variations in the significant applied-stress value, and for the same component as in FIGS. 2 and 3.

The tendency of maximum value MBNmax to increase with increasing significant values σ is shown in FIG. 3. This dependence on significant values a was observed by the Applicant in the coercive point nonhysteretic differential susceptibility χ'an(H=0) of AISI 4130 steel, as shown in FIG. 4.

More specifically, coercive point nonhysteretic differential susceptibility χ'an(H=0) is the nonhysteretic differential susceptibility χ'$_{an}$ measured with zero magnetic field amplitude H, and when residual magnetization remains, due to the hysteresis cycle of the component.

The equation showing this relationship between significant stress value σ and coercive point nonhysteretic differential susceptibility χ'an(H=0)—i.e. with zero amplitude H—was obtained from the Langevin function for magnetization in which the equivalent stress field Hσ was added to the applied magnetic field H and to the internal coupling field αM.

The Langevin function used to represent nonhysteretic magnetization M$_{an}$ is:

$$M_{an}(H) = M_s\left\{\coth\left(\frac{H+\alpha M}{a}\right) - \left(\frac{a}{H+\alpha M}\right)\right\}, \quad (4)$$

where M$_s$ is saturation magnetization, i.e. the maximum magnetization the material of component 2 can attain; and a is a shape parameter that factors in temperature and the size of the magnetic domains of the material of component 2.

Bearing in mind the effect of equivalent magnetic field Hσ (Eq. 3), the nonhysteretic magnetization M$_{an}$ equation, in the presence of stress, becomes:

$$M_{an}(H) = M_s\left\{\coth\left(\frac{H+\alpha M + H_\sigma}{a}\right) - \left(\frac{a}{H+\alpha M + H_\sigma}\right)\right\} \quad (5)$$

Magnetostriction at lower magnetization values, in which λ is symmetrical in M, may be approximated:

$$\lambda = bM^2 \quad (6)$$

so that:

$$\frac{d\lambda}{dM} = 2bM \quad (7)$$

The value of magnetostriction coefficient b may be determined experimentally by magnetostriction measurements. Nonhysteretic magnetization is originally linear with respect to amplitude H, and may be expressed by the equation:

$$\frac{M_{an}(H)}{M_s} = \left(\frac{H + \left(\alpha + \frac{3b\sigma}{\mu_0}\right)M_{an}(H)}{3a}\right) \quad (8)$$

for low H values. This gives an original differential susceptibility equation of:

$$[\chi'_{an}(\sigma)]_{H=0} = \frac{M_s}{3a - \left(a + \frac{3b\sigma}{\mu_0}\right)M_s} \quad (9)$$

which may be rewritten in the form of:

$$\frac{1}{[\chi'_{an}(0)]_{H=0}} - \frac{1}{[\chi'_{an}(\sigma)]_{H=0}} = \frac{3b\sigma}{\mu_0} \quad (10)$$

Using the nonhysteretic differential susceptibility χ'an (H=0) test data of different significant values σ and zero amplitude H, and magnetostriction coefficient value b, it has been possible to calculate, for AISI 4130 steel, the dependence of nonhysteretic differential susceptibility χ'an(H=0), with zero magnetic field amplitude H, on significant stress value σ. The Applicant has also observed that, for many materials, maximum nonhysteretic differential susceptibility χ'an(H=0) equals maximum differential susceptibility χ'max at the coercive point, i.e. with zero amplitude H.

On the basis of equation (10), maximum differential susceptibility χ'max, normally measured at the coercive point, is therefore related to significant stress value σ by the equation:

$$\frac{1}{[\chi'_{max}(0)]} - \frac{1}{[\chi'_{max}(\sigma)]} = \frac{3b\sigma}{\mu_0} \quad (11)$$

The truth of the theory was confirmed by plotting the reciprocal of nonhysteretic differential susceptibility χ'$_{an}$ versus significant stress value σ, as shown in FIG. 5.

As shown in FIG. 5, the theoretical prediction represented by the linear relation agrees with the tendency shown in the measurements, thus confirming the linear relation in equation (11) as a convenient way of determining significant stress value σ from a magnetic property of measurable volume—in particular, maximum differential susceptibility χ'max in the absence of stress. An alternative and often more practical option is to use maximum differential susceptibility $\chi'\mathrm{max}$ at the coercive point, as shown in equation (11).

The Applicant has observed that maximum value MBNmax varies with significant stress value σ in the same way as maximum differential susceptibility $\chi'\mathrm{max}$.

Some relationship must therefore exist between these two results. One theory is that both correspond to the same phase in the magnetizing process, in which the values of dM/dH and therefore dB/dH are maximum. These regions are represented by the steepest slope of the magnetization curve at the coercive point. Another theory is that the level of Barkhausen activity in a given time interval dMJS/dt is proportional to the rate of change in magnetization dM/dt= (dM/dH) (dH/dt)=$\chi'$dH/dt. This relationship has already been described in the Barkhausen micrometric activity model on the basis of the hysteresis theory. According to this model, the sum of the voltages generated by Barkhausen noise in a given period Δt is proportional to the total change in magnetization ΔM over the same period. This can be expressed by the equation:

$$M_{JS} = \gamma \Delta M = \gamma \left(\frac{dM}{dt}\right) \Delta t \qquad (12)$$
$$= \gamma \left(\frac{dM}{dH}\right)\left(\frac{dH}{dt}\right) \Delta t = \gamma \chi' \left(\frac{dH}{dt}\right)(\Delta t)$$

where γ is merely a proportion coefficient (0≤γ≤1) representing the ratio of discontinuous to total variation in magnetization. This equation defines the link between effective value MBN and differential susceptibility $\chi'$ at any point in the hysteresis cycle, and so confirms the direct relationship between maximum value MBNmax and maximum differential susceptibility $\chi'\mathrm{max}$. The graph of reciprocal 1/MBNmax may therefore also be represented as a linear relation of significant applied-stress value σ, as shown in FIG. 5.

Figure 6:
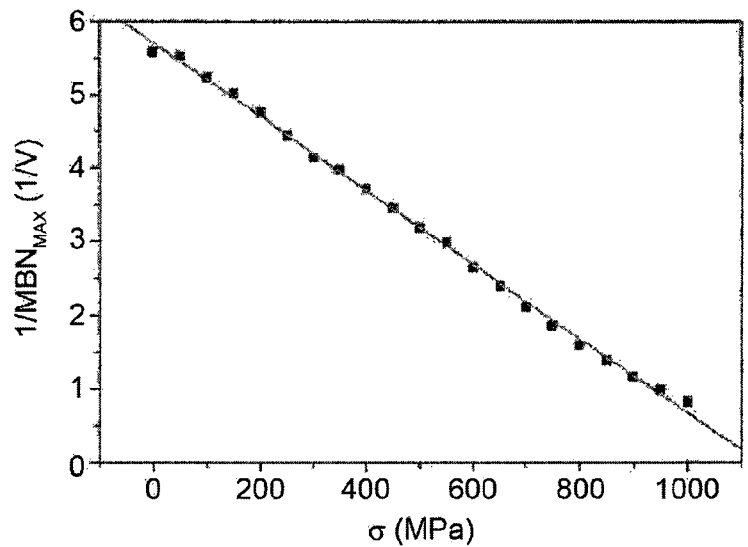
FIG. 6 shows a theoretical test graph of the reciprocal of the maximum effective Barkhausen noise signal value alongside variations in the significant applied-stress value, and for the same component as in FIGS. 2 to 5.
Figure 7:
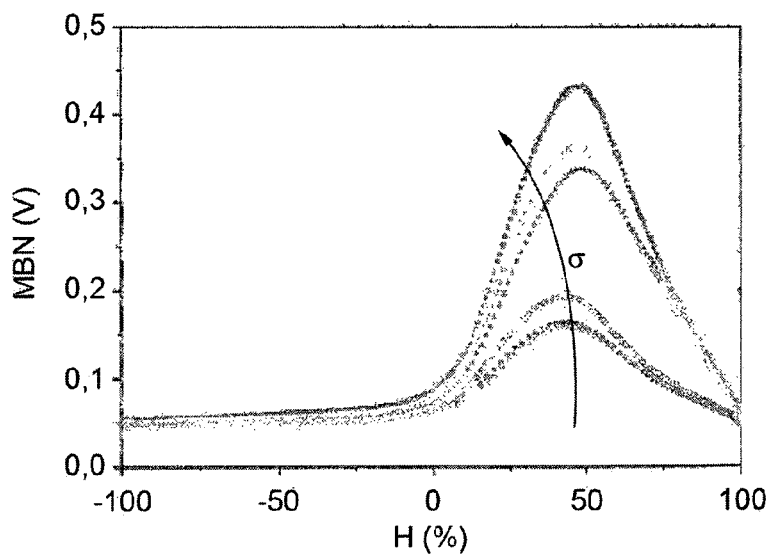
FIGS. 7 and 8 show graphs of the effective Barkhausen noise signal value alongside variations in the strength of the magnetic field applied by the FIG. 1 system, and in a significant residual-stress value, for respective components of different materials.
Figure 8:
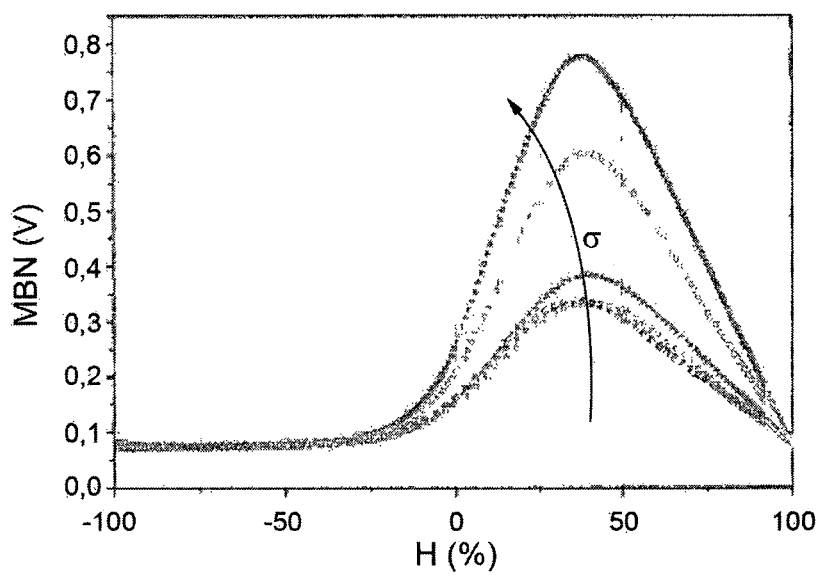

For both groups of test-pieces, effective values MBN versus significant residual-stress value a are shown in FIGS. 6 and 7.

The advantages of system 1 and the method according to the present invention will be clear from the above description.

In particular, they employ a linear relation between the reciprocal 1/MBNmax of maximum value MBNmax of effective value MBN and significant applied- or residual-stress value σ.

As such, system 1 and the method according to the present invention provide for easily and objectively determining significant value σ. More specifically, when component 2 is made of nitrided or carburized steel, and has been shot peened and ground above tempering temperature, system 1 provides for accurately determining residual stress in the regions directly beneath surface 8 of component 2.

Moreover, by generating the magnetic field at various frequencies f1, f2, . . . , fi, . . . , fn, system 1 and the method according to the invention provide for determining significant value a at different distances d1, d2, . . . , di, . . . , dn from surface 8.

Finally, system 1 and the method according to the invention provide for subtracting, from the effective value MBN determined at a frequency fi, i.e. associated with distance di from surface 8, the effective value MBN determined at frequencies f1, f2, . . . , fi-1.

As such, system 1 and the method according to the invention provide for easily factoring in attenuation by the material of component 2, with no need for complex mathematical calculations requiring greater computing power.

Clearly, changes may be made to system 1 and the method as described herein without, however, departing from the scope of the accompanying Claims.

The invention claimed is:

1. A system for determining a significant stress value of a component made of magnetizable material, the system comprising:
    a U-shaped magnetic field generator comprising (i) two parallel arms with respective ends positioned perpendicular to a free surface of said component and configured to contact said free surface; (ii) a crosspiece extending between said arms, wherein said crosspiece is parallel to and a predetermined distance from said free surface; and (iii) a ferrite core having a first winding connected to an alternating-current generator, wherein said U-shaped magnetic field generator is configured to generate a magnetic field having a varying amplitude in said component, thereby inducing voltage pulses in the first winding;
    an amplifier configured to amplify said voltage pulses to generate a Barkhausen noise signal of said component;
    a pickup unit comprising a second winding, wherein the pickup unit is configured to acquire said Barkhausen noise signal and variations in said varying amplitude of said magnetic field in said component;
    a processing unit configured to process said Barkhausen noise signal acquired by the pickup unit and to calculate, based on said Barkhausen noise signal, the significant stress value of said component, a reciprocal of a maximum value of said Barkhausen noise signal and variations in said amplitude of said magnetic field;
    a memory unit configured to store a linear relation between said reciprocal of said maximum value and said significant stress value; and
    a display configured to display said significant stress value representing residual stress within said component.

2. A system as claimed in claim 1, further comprising a band-pass filter that is configured to filter said Barkhausen noise signal downstream from said pickup unit and upstream from said memory unit.

3. A system as claimed in claim 2, wherein said magnetic field generator is configured to generate said magnetic field at at least a first frequency associated with a first distance from said free surface of said component; and
    further wherein components of said Barkhausen noise signal having frequencies between said first frequency and a threshold frequency (f0) independent of said distance pass through said band-pass filter.

4. A system as claimed in claim 3, wherein said magnetic field generator is further configured to generate said magnetic field at at least a second frequency associated with a second distance from said free surface of said component; and
    further wherein said memory unit stores a first and second said linear relation associated with said first and second frequency respectively, and associated with said significant stress value at said first and second distance respectively from said free surface of said component.

5. A system as claimed in claim 4, wherein said magnetic field generator is configured to generate said magnetic field in a range of frequencies associated with increasing distances from said surface; and
    further wherein said processing unit comprises an analysis unit which subtracts, from said Barkhausen noise signal acquired at a given distance, a value representing Barkhausen noise signals acquired at distances smaller than said given distance.

6. A system as claimed in claim 5, wherein said analysis unit subtracts, from said Barkhausen noise signal acquired at said given distance, said Barkhausen noise signal acquired at the distance preceding said given distance.

7. A system as claimed in claim 1, wherein said memory unit is further configured to store:
   a first linear relation between said reciprocal of said maximum value and a significant applied-stress value, and variations in said amplitude, and for a given frequency; and
   a second linear relation between said reciprocal of said maximum value and a significant residual-stress value, and variations in said amplitude, and for a given frequency.

8. A system as claimed in claim 7, wherein angular coefficients of said first and second linear relation are equal for components made of the same material.

9. A method of determining stress of a component made of magnetizable material, the method comprising the steps of:
   generating, by a U-shaped magnetic field generator, a magnetic field having a varying amplitude in said component, wherein said U-shaped magnetic field generator comprises (i) two parallel arms with respective ends perpendicular to a free surface of said component and configured to contact said free surface, (ii) a crosspiece extending between said arms, wherein said crosspiece is parallel to and a predetermined distance from said free surface; and (iii) a ferrite core having a first winding connected to an alternating-current generator, and whereby the magnetic field induces voltage pulses in the first winding;
   amplifying, by an amplifier, said voltage pulses to generate a Barkhausen noise signal of said component;
   acquiring, by a pickup unit comprising a second winding, said Barkhausen noise signal of said component and variations in said varying amplitude of said magnetic field in said component;
   processing, by a processing unit that includes a memory unit, said Barkhausen noise signal acquired by the pickup unit;
   calculating, by said processing unit, a reciprocal of a maximum value of said Barkhausen noise signal, and variations in said amplitude of said magnetic field in said component;
   calculating, by the processing unit, a significant stress value of said component as a function of a linear relation between said reciprocal of the maximum value and said significant stress value; and
   displaying, by a display, said significant stress value representing residual stress within said component.

10. A method as claimed in claim 9, further comprising the step of filtering, by a band-pass filter, said Barkhausen noise signal prior to said calculating steps and after said acquiring step.

11. A method as claimed in claim 10, wherein said generating step comprises generating, by said magnetic field generator, said magnetic field at a first frequency associated with a first distance from a free surface of said component; and
   further wherein said filtering step comprises filtering, by said band-pass filter, a band of frequencies of said signal between said first frequency and a threshold frequency, independent of said first distance.

12. A method as claimed in claim 11, wherein said generating step further comprises generating, by said magnetic field generator, said magnetic field at a second frequency; and
   further comprising storing, in said memory unit, a first and second said linear relation associated with said first frequency and a second frequency, respectively, and associated with said significant stress value at said first distance and a second distance, respectively from said surface of said component.

13. A method as claimed in claim 12, wherein said generating step further comprises generating, by said magnetic field generator, said magnetic field at a range of frequencies associated with increasing distances from said surface; and
   said calculating step further comprises subtracting, from said Barkhausen noise signal acquired at a given distance, said Barkhausen noise signal acquired at a distance smaller than the given distance (di).

14. A method as claimed in claim 9, further comprising a step of calibrating, in which said linear relation is calculated; said calibrating step comprising:
   applying a load to said component to generate stress in said component;
   measuring said significant stress value by x-ray diffractometry; and
   determining said reciprocal of the maximum value of said Barkhausen noise signal at each said significant stress value.

* * * * *